(12) United States Patent (10) Patent No.: US 8,803,087 B2
Fukuyama et al. (45) Date of Patent: Aug. 12, 2014

(54) SPECTRUM ANALYZER AND METHOD OF SPECTRUM ANALYSIS

(75) Inventors: Hirofumi Fukuyama, Takasago (JP); Shoichi Mure, Takasago (JP)

(73) Assignee: Kobe Steel, Ltd., Kobe-shi (JP)

( * ) Notice: Subject to any disclaimer, the term of this patent is extended or adjusted under 35 U.S.C. 154(b) by 1351 days.

(21) Appl. No.: 11/230,633

(22) Filed: Sep. 21, 2005

(65) Prior Publication Data

US 2006/0065831 A1 Mar. 30, 2006

(30) Foreign Application Priority Data

Sep. 30, 2004 (JP) ................................. 2004-286495

(51) Int. Cl.
*G21K 7/00* (2006.01)
*G01N 23/20* (2006.01)
(52) U.S. Cl.
CPC ...................................... *G01N 23/20* (2013.01)
USPC ............................ 250/309; 250/305; 250/307
(58) Field of Classification Search
CPC ....................................................... G21K 7/00
USPC .......................................................... 250/309
See application file for complete search history.

(56) References Cited

U.S. PATENT DOCUMENTS

| 3,480,774 | A | * | 11/1969 | Smith | ............................ | 850/14 |
| 5,637,870 | A | * | 6/1997 | Tanigaki | ........................ | 850/18 |
| 6,735,556 | B2 | * | 5/2004 | Copel | ............................... | 703/2 |

FOREIGN PATENT DOCUMENTS

| JP | 2-156145 | 6/1990 |
| JP | 2003-344319 | 12/2003 |
| JP | 2004-20459 | 1/2004 |
| JP | 2004-191222 | 7/2004 |

OTHER PUBLICATIONS

Yoshikazu Mori, et al. "A High Resolution RBS System", R&D Kobe Steel Engineering Reports, vol. 52, No. 2, Sep. 2002, pp. 53 to 56.

* cited by examiner

*Primary Examiner* — Phillip A Johnston
(74) *Attorney, Agent, or Firm* — Oblon, Spivak, McClelland, Maier & Neustadt, L.L.P.

(57) ABSTRACT

A spectrum analysis method is provided in which a composition distribution of a sample in the depth direction is analyzed based on an energy spectrum of scattered particles scattered at the sample by irradiation with ion beams, the sample being composed of a single layer or multiple layers. In the spectrum analysis, the thickness of an object layer of the sample is obtained by the steps of measuring an energy spectrum of scattered particles scattered in a scattering angle (specific scattering angle) direction at which an energy spectrum corresponding to the object layer independently appears, extracting an independent energy spectrum of the object layer which independently appears in the measured energy spectrum, and calculating the thickness of the object layer based on a spectrum area surrounded by the waveform of the independent energy spectrum thus extracted. Since the thickness of the object layer is analyzed based on the spectrum area instead of using the half value width of the spectrum, the analysis processing can be rapidly performed and the accuracy of the analysis can be improved.

7 Claims, 10 Drawing Sheets

SPECTRUM ANALYZER AND METHOD OF SPECTRUM ANALYSIS

BACKGROUND OF THE INVENTION

1. Field of the Invention

The present invention relates to a spectrum analysis technique of Rutherford backscattering spectrometry and the like, and more particularly, relates to a spectrum analyzer and a spectrum analysis method, accurately analyzing a composition distribution of a sample in the depth direction by measurement of an energy spectrum of scattered ions scattered from the sample which is composed of a single layer or multiple layers.

2. Description of the Related Art

Heretofore, in the fields of semiconductor techniques, crystal thin film techniques and the like, as a method for analyzing a sample such as a semiconductor device having a film structure composed of a single layer or multiple layers, various sample analysis methods such as Rutherford backscattering spectrometry (hereinafter referred to as "RBS method") and Elastic recoil detection (hereinafter referred to as "ERD method") have been widely used.

As a particular method for analyzing the concentration of a sample having an unknown composition distribution in the depth direction by using the above RBS method, a fitting method disclosed in Japanese Unexamined Patent Application Publication No. 2004-191222 may be mentioned by way of example. In this fitting method, after a theoretical energy spectrum (hereinafter referred to as "theoretical spectrum") is calculated while an assumed composition distribution of a sample in the depth direction, which is assumed beforehand, is being changed, this calculated theoretical spectrum is compared with a measured energy spectrum (hereinafter referred to as "measured spectrum") measured by a RBS analyzer using the RBS method described above, and the assumed distribution is searched in a trial and error manner so that the above two spectra coincide with each other, thereby determining the composition distribution of the sample in the depth direction. In addition to a sample having an unknown composition distribution, the analysis method described above may also be applied to a thickness analysis of a specific layer of a known sample.

However, in the fitting method described above, since the search of the assumed distribution is performed sensuously based on the knowledge, experience, and/or technique of a person conducting the analysis so that the theoretical spectrum and the measured spectrum coincide with each other, the analysis itself may depend on the personal capacity to a certain extent in many cases. Hence, due to individual differences, the analysis speed, analysis time, and analysis accuracy may vary.

Incidentally, in recent years, a high resolution sample-analyzer was developed which effectively analyzes the composition distribution of a sample in the depth direction without using the above fitting method, the method being disclosed in many papers such as Japanese Unexamined Patent Application Publication Nos. 2004-20459 and 2003-344319, and "High resolution RBS system" by Yoshikazu. Mori et al., Kobe Steel Technical Bulletin, R & D, Vol. 52, No. 2, pp. 53 to 56 issued on Sep. 1, 2002.

Figure 1:
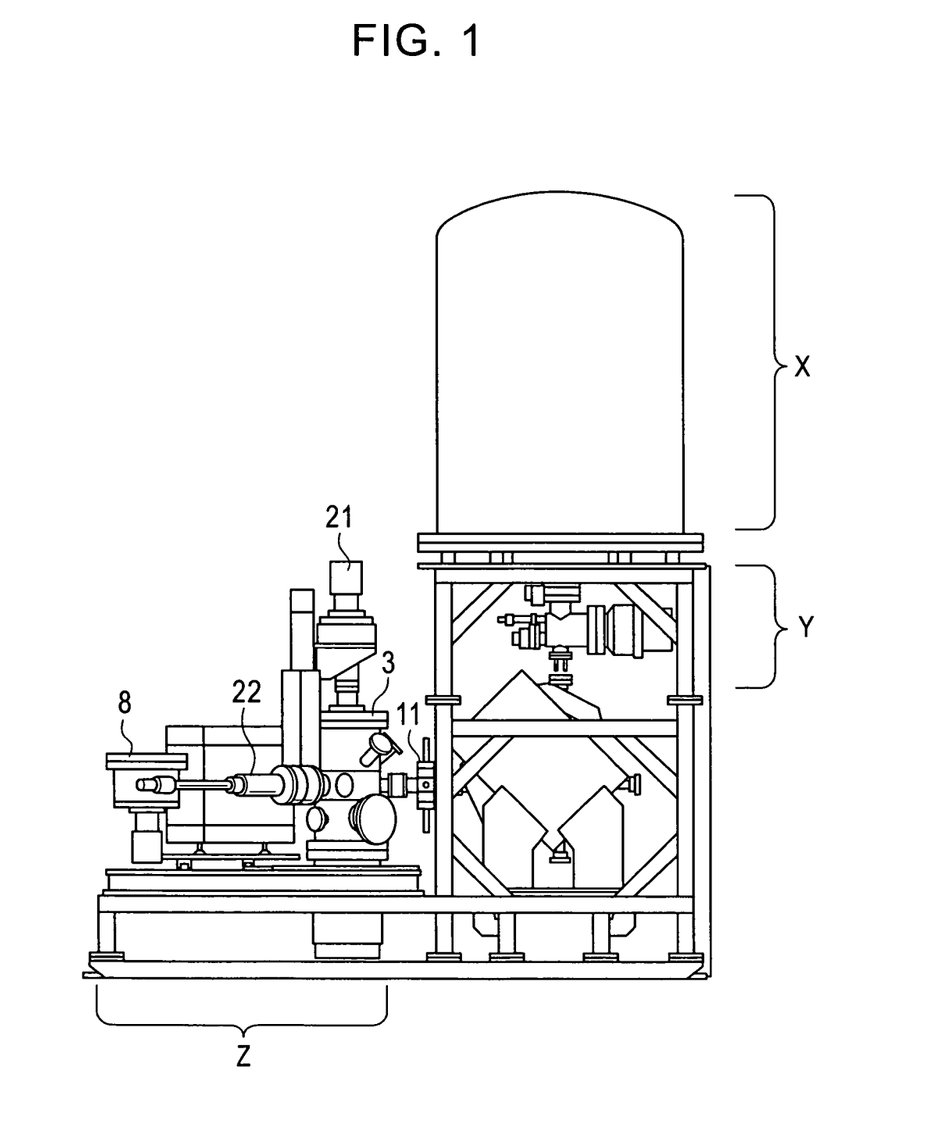
FIG. 1 is a schematic view of the entire structure of a HRBS analyzer A to which a spectrum analysis method according to an embodiment of the present invention is applied.
Figure 2:
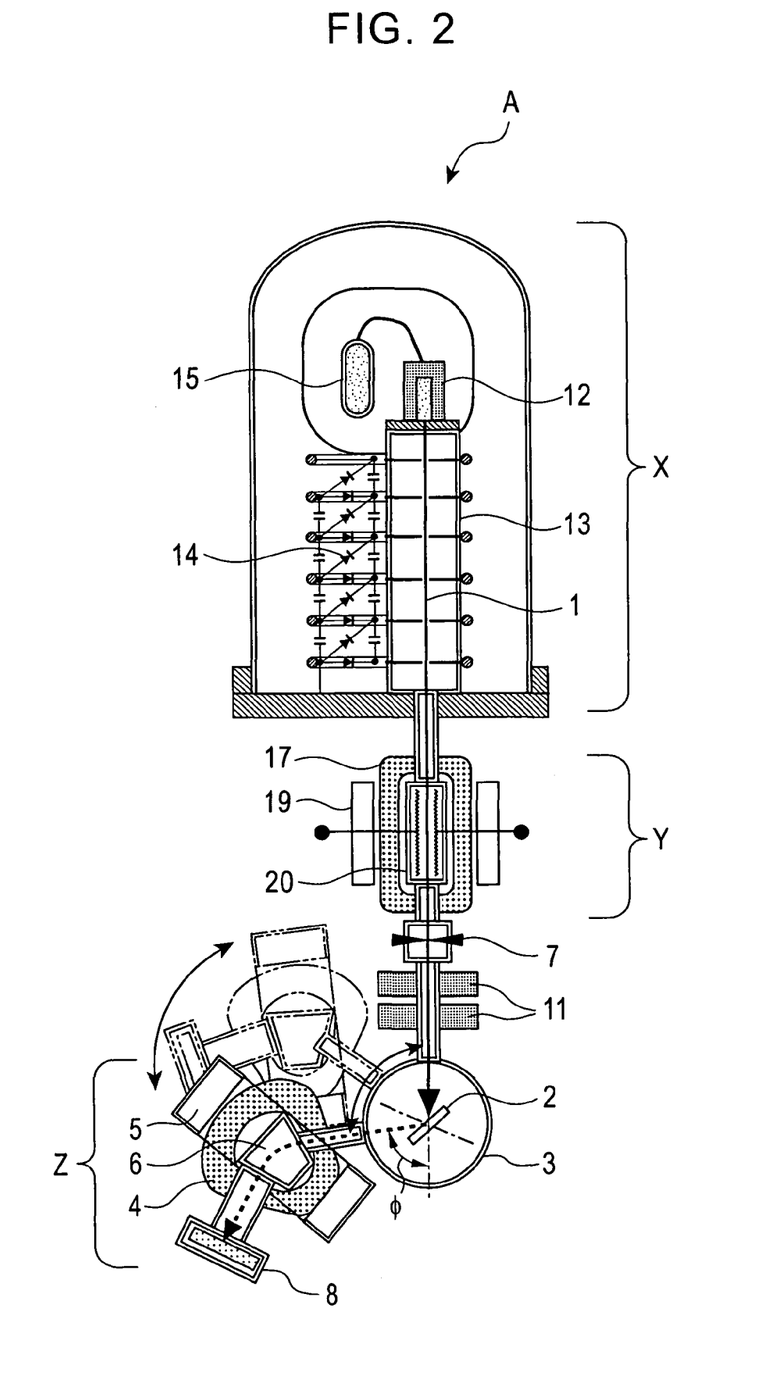
FIG. 2 is a schematic view showing constituent elements of the HRBS analyzer A.

Referring to FIGS. 1 and 2, the structure and functions of a high resolution RBS analyzer (hereinafter referred to as "HRBS analyzer") A, which is one example of the above high resolution sample analyzer, will be briefly described. FIG. 1 is a schematic view showing the entire structure of the HRBS analyzer A, and FIG. 2 is a schematic view showing individual constituent elements of the HRBS analyzer A.

As shown in FIGS. 1 and 2, the HRBS analyzer A described above has a basic structure composed of an ion beam generator X, a Wien filter Y provided with a slit 7 (see FIG. 2), a quadrupole lens 11, a vacuum container 3 in which a sample 2 to be analyzed is placed, and an electromagnetic spectrometer Z measuring an energy spectrum of scattered ions (one example of scattered particles) scattered from the surface of the sample 2. Reference numeral 21 shown in FIG. 1 indicates a goniometer which changes the angle of ion beams incident onto the sample by changing the position of the sample placed in the vacuum container 3, and reference numeral 22 indicates a transfer rod carrying the sample in and out of the vacuum container 3.

The ion beam generator X described above accelerates light ions, which are generated by an ion source 12 using a gas (such as a helium gas) supplied from a cylinder 15, by a high voltage supplied from a Cockcroft type high voltage circuit 14 so as to have a constant energy in an acceleration tube 13, and irradiation of the ions thus accelerated is then performed. The Wien filter Y and the slit 7 described above cooperatively extract specific ions (such as monovalent helium ions) from ion beams 1 which are accelerated and irradiated by the ion beam generator X. The Wien filter Y is a filter formed so that the deflection (proportional to the kinetic momentum of ions) caused by a magnetic field generated by a magnetic pole 17, a coil 18, and a return yoke 19 and the deflection (proportional to the energy of ions) caused by an electrical field generated by parallel electrodes 20 work in opposite directions to each other with respect to ions passing through the Wien filter Y. Hence, in the Wien filter Y described above, specific ions (such as helium monovalent ions) of the ion beams 1 are allowed to travel straight, and the trajectories of the other ions (such as divalent helium ions and hydrogen ions) are curved. By the above characteristics of the Wien filter Y, all the ions except the specific ions used for analysis cannot pass through the slit 7 and are eliminated, the slit 7 being provided at the downstream side of the Wien filter Y along the incident direction of the ion beams so as to only allow ions traveling straight to pass through the slit 7. As described above, the specific ions extracted from the ion beams 1 are converged by the quadrupole lens 11 provided at the downstream side of the slit 7 along the incident angle direction of the ion beams, and a predetermined beam spot is then irradiated onto the surface of the sample 2. The specific ions irradiated onto the surface of the sample 2 are scattered thereon, and some of the scattered ions are incident onto the electromagnetic spectrometer Z. This electromagnetic spectrometer Z deflects scattered ions passing therethrough by a magnetic field generated by a coil 4, a return yoke 5, and a magnetic pole 6 in accordance with the energy of the scattered ions and then guides them to a detector 8. The detector 8 is an energy sensitive type ion detector using a semiconductor such as silicon or germanium and has a plurality of channels. In this detector 8, when the positions (deflection by the magnetic field) of the channels to which the scattered ions are guided are detected, the detection signals are sent to a computer (or simulator) not shown in the figure, and the number of the scattered ion counts is measured. The positions and the number of the scattered ion counts thus obtained are used for calculating (measuring) an energy spectrum of the scattered ions scattered from the surface and the inside of the sample 2 by the above computer.

Figure 3:
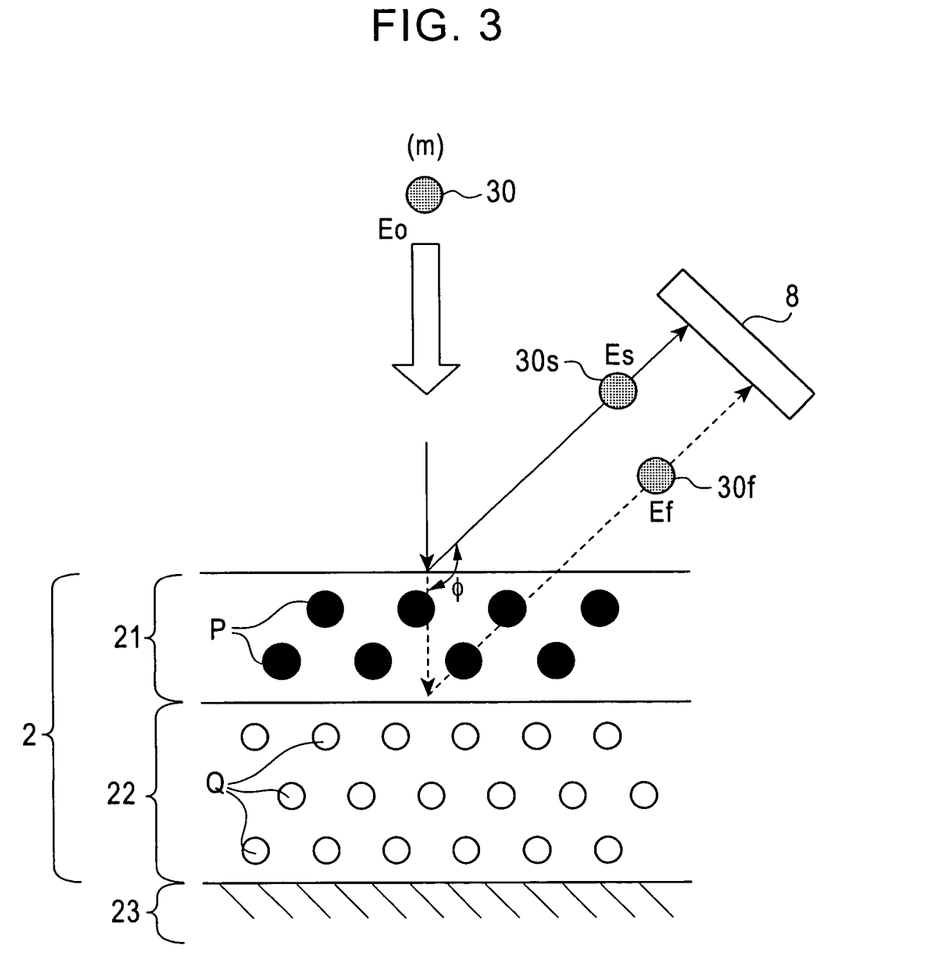
FIG. 3 is a view illustrating the basic principle of a method for analyzing a composition distribution such as the thickness of a sample based on an energy spectrum.

Next, referring to FIG. 3, the basic principle of a related analysis method will be described which analyzes the composition distribution such as the thickness of a sample based on a measured energy spectrum of the scattered ions. As shown in FIG. 3, the sample 2 has a two-layered thin film structure formed of a layer 21 composed of a heavy element P having mass number M1 and a layer 22 composed of a light element Q having mass number M2 provided in that order from the top. In this figure, reference numeral 23 (oblique line portion) indicates a silicon substrate holding the sample 2.

When an ion 30 (hereinafter referred to as "incident ion") emitted from the ion beam generator X toward the sample 2 is irradiated onto the sample 2, followed by collision with component atoms (composition elements) of the sample 2, this collision may be substantially regarded as the elastic scattering. Hence, as shown in FIG. 3, for example, when the incident ion 30 having energy Eo and mass number m collides with the element P present at the surface of the layer 21 of the sample 2 and is then reflected by the elastic scattering in the direction of a scattering angle (detection angle) $\phi$, energy Es of a scattered ion 30s thus reflected is given by equation (1) below based on the law of conservation of momentum.

$$E_1 = K \cdot E_0 \qquad (1)$$

$$K = \left\{ \frac{\sqrt{M_1^2 - (m \cdot \sin\phi)^2} + m \cdot \cos\phi}{M_1 + m} \right\}^2 \qquad (2)$$

In the above equation, K is called a kinematic factor (hereinafter referred to as "K factor") and is a coefficient representing the rate of energy loss at the collision of the incident ion 30. This K factor is represented as a function of mass number m of the incident ion 30 and mass number M1 of the collision ion P which collides with the ion 30, and from the energy Es of the scattered ion 30s, the mass number of the collision ion can be obtained.

In addition, when the incident ion 30 collides at a depth $\Delta t$ apart from the surface of the layer 21 of the sample 2 and is then scattered, the energy of the ion 30 is attenuated by an electron cloud (free electron group traveling around the atomic nucleus of an element) while the incident ion 30 reaches the collision element and then jumps out of the surface of the sample after making the elastic collision. Hence, energy Ef of a scattered ion 30f reflected at the depth $\Delta t$ and the energy Es of the scattered ion 30s scattered at the surface of the sample have the following relationship represented by equation (3).

$$E_s - E_f = \Delta E \qquad (3)$$

In addition, it has been known that $\Delta E$ is linearly proportional to the distance through which the ion travels, and when the attenuation coefficient (called stopping coefficient in some cases) of the energy of the incident ion 30 and the element number density of an element of the sample are represented by $\epsilon$ and N, respectively, $\Delta E$ of equation (3) can be represented by equation (4) below. The stopping coefficient $\epsilon$ is a function of energy E and charge Z of the sample. In addition, the stopping coefficient $\epsilon$ and the element number density N can both be treated as predefined physical quantities as long as the elements and the compositional structures of the layers 21 and 22 forming the sample 2 are known.

$$\Delta E = \epsilon N \Delta t \qquad (4)$$

Figure 4:
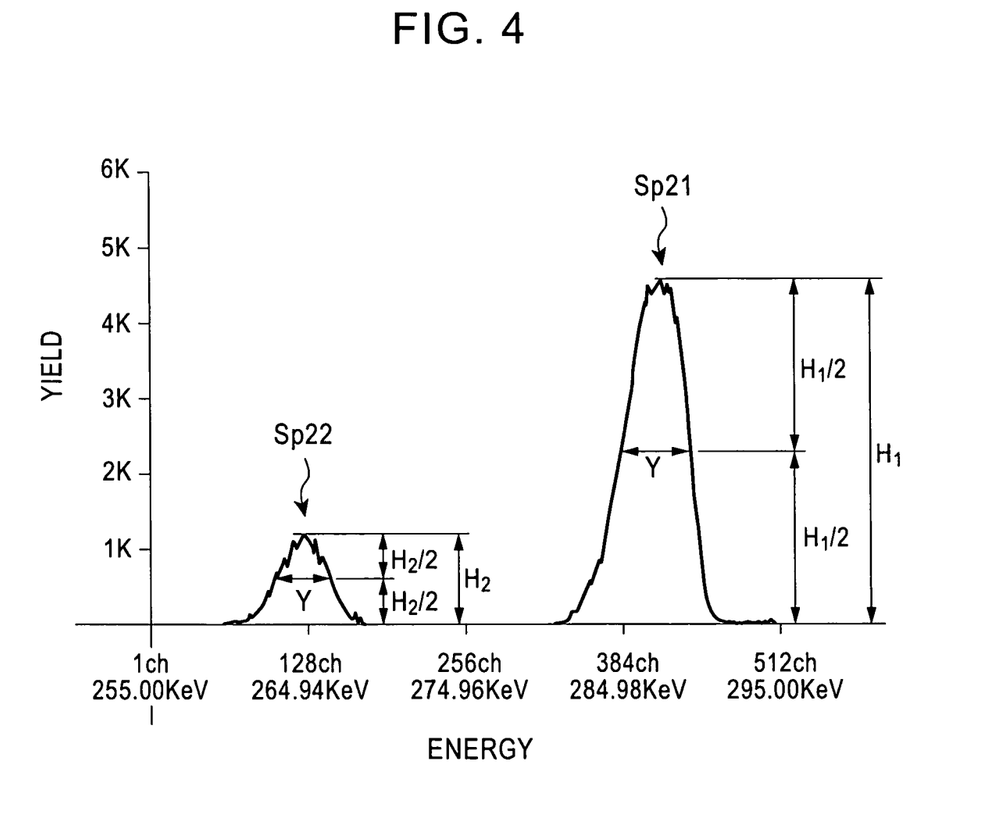
FIG. 4 is a spectrum view showing one example of an energy spectrum obtained when a sample 2 shown in FIG. 3 is irradiated with ion beams.

In FIG. 4, one example of an energy spectrum is shown which is obtained when ions having a predetermined energy are irradiated onto the sample 2 shown in FIG. 3. In FIG. 4, reference numeral Sp21 indicates a measured spectrum of the layer 21 of the sample 2, and reference numeral Sp22 indicates a measured spectrum of the layer 22.

In the measured spectra Sp21 and Sp22 thus measured, the widths of Sp21 and Sp22 each represent the energy attenuation $\Delta E$. However, as shown in FIG. 4, since the measured spectrum has a Gauss distribution, the width of the measured spectrum cannot be easily specified. Hence, a spectrum width (a so-called half value width) at a half of the maximum value (H1 and H2 in FIG. 4) of the yield (the number of scattered ions counts detected by the detector) of the measured spectrum is regarded as the energy attenuation $\Delta E$ shown by a double sided arrow in the figure, and the thickness of an object layer to be analyzed is then obtained.

When a sample or a layer to be analyzed (hereinafter referred to as an "object sample" or "object layer", respectively) is relatively thick, when the incident energy is high, or when the measurement is performed for a long period of time, a sufficient number of scattered ion counts can be measured. Accordingly, even when the above related analysis method is used, the thickness of the object layer or the composition of the object sample may be accurately calculated or analyzed when the half value width is regarded as the energy attenuation $\Delta E$. However, when the object sample or the object layer is very thin, the incident energy is low, or the measurement is not allowed to be conducted for a long period of time, by the above HRBS analyzer A, a count value (spectrum) sufficient for highly accurate measurement cannot be obtained. Hence, in the case described above, when the related analysis method in which the layer thickness or the composition distribution is obtained based on the above half value width is performed, problems may arise in that the analysis result contains errors or varies. By the problem described above, when the object sample or the object layer is extremely thin, for the analysis of the thickness and/or the composition thereof, the fitting method described above must still be performed.

In addition, in the case of a multilayer structure, although depending on the scattering angle, the measured spectrum is obtained as an overlapping spectrum in which layer spectra of respective layers are overlapped with each other, that is, in which the spectra of the respective layers are not independently observed; hence, by the related analysis method described above, the spectrum of the object layer cannot be easily extracted, and as a result, there may be a problem in that the thickness and/or the composition of the object layer cannot be easily analyzed from the measured spectrum. This problem is also a problem which may probably occur in the analysis by the above fitting method.

SUMMARY OF THE INVENTION

Hence, in consideration of the situations described above, the present invention was made, and an object of the present invention is to provide a spectrum analysis method and a spectrum analyzer, capable of decreasing the time required for analysis and improving the analysis accuracy by analyzing the thickness of an object layer using the spectrum area thereof instead of the half value width of the spectrum.

In accordance with one aspect of the present invention, there is provided a spectrum analyzer analyzing a composition distribution of a sample in the depth direction based on an energy spectrum of scattered particles scattered at the sample by irradiation with ion beams, the sample including at least one object layer to be analyzed which contains at least one element. The spectrum analyzer. described above comprises: an ion beam generator; scattering angle-setting means for setting a scattering angle of ion beams which are emitted from the ion beam generator and which are scattered at the sample; measured spectrum-obtaining means for obtaining a measured energy spectrum by measuring energy of scattered particles scattered in the direction of the scattering angle set by the scattering angle-setting means, the scattered particles being scattered from the sample when the sample is irradiated with the ion beams; independent spectrum-extraction means for extracting an independent energy spectrum of said at least one element of the object layer which independently appears in the measured energy spectrum obtained by the measured spectrum-obtaining means; and layer thickness-calculation means for calculating the thickness of the object layer based on a spectrum area surrounded by the waveform of the independent energy spectrum extracted by the independent spectrum-extraction means.

In the spectrum analyzer described above, the scattering angle-setting means may comprise: a simulator for obtaining theoretical spectra at scattering angles designated for the sample; and scattering angle-determining means for determining the scattering angle based on the theoretical spectra obtained by the simulator.

Furthermore, the scattering angle-determining means may comprises: theoretical spectrum-display means for displaying the theoretical spectra; and input means for performing input to select one of the theoretical spectra displayed by the theoretical spectrum-display means.

In accordance with another aspect of the present invention, there is provided a spectrum analysis method for analyzing a composition distribution of a sample in the depth direction based on an energy spectrum of scattered particles scattered at the sample by irradiation with ion beams, the sample including at least one object layer to be analyzed. The spectrum analysis method described above comprises: a measured spectrum-obtaining step of obtaining a measured energy spectrum by measuring energy of scattered particles scattered in the direction of a specific scattering angle at which an energy spectrum corresponding to the object layer independently appears; an independent spectrum-extraction step of extracting an independent energy spectrum of the object layer which independently appears in the measured energy spectrum obtained by the measured spectrum-obtaining step; and a layer thickness-calculation step of calculating the thickness of the object layer based on a spectrum area surrounded by the waveform of the independent energy spectrum extracted by the independent spectrum-extraction step.

In the spectrum analysis method described above, the specific scattering angle may be searched by a process comprising: a theoretical spectrum-obtaining step of obtaining theoretical energy spectra corresponding to predetermined scattering angles of the scattered particles by simulation based on a predefined distribution set beforehand for the sample in the depth direction; and a scattering angle-searching step of searching the scattering angle at which the energy spectrum corresponding to the object layer independently appears in the theoretical energy spectra obtained by the theoretical spectrum-obtaining step.

Since the measured spectrum reflects the number of atoms (number of elements) contained in the sample, it may be said that the spectrum area represents the number of elements distributed in the depth direction of the sample. Accordingly, instead of using the half value width, when the thickness analysis is performed using the spectrum area described above, it is more advantageous in terms of the analysis accuracy. In addition, even in the case of a thin film layer or a thin film sample having a small number of counts (measured yield), analysis having a high accuracy can be realized. Furthermore, without using the fitting method which depends on personal knowledge, experience, and the like, since the thickness of the object layer can be calculated by simulation using a computer (simulator), processing capacity in the entire analysis can be improved.

It has been known that the measured spectrum shows different patterns depending on the scattering angle. In addition, it has also been known that when the composition distribution (corresponding to the predefined distribution) of a sample in the depth direction is understood beforehand, theoretical spectra at respective scattering angles corresponding to the predefined distribution can be calculated by simulation.

Hence, in the present invention, the specific scattering angle is preferably obtained by the steps of obtaining theoretical energy spectra corresponding to predetermined scattering angles of scattered ions by simulation based on the predefined distribution set beforehand for the sample in the depth direction, and then searching a scattering angle at which an energy spectrum corresponding to the object layer independently appears in the obtained theoretical energy spectra.

From the theoretical spectra at a plurality of scattering angles corresponding to the above predefined distribution, a scattering angle (called a specific scattering angle) at which the independent spectrum appears can be easily found out by simulation. Hence, when specific scattering angles corresponding to estimated composition distributions (predefined distribution) of samples are searched beforehand, time and labor required for searching the specific scattering angle can be reduced at each time when a new sample is analyzed.

When the object layer is composed of a plurality of elements, a plurality of spectra is measured from the object layer. Hence, in this case, based on the spectrum areas surrounded by the waveforms of the independent energy spectra of the respective elements, the thickness of the objective layer is preferably calculated. As described above, since the layer thickness is obtained based on the plurality of spectra, the analysis accuracy can be improved.

In addition, by comparing the spectrum area surrounded by the waveform of the independent spectrum described above with that surrounded by the waveform of a standard spectrum obtained beforehand, the thickness of the object layer may also be obtained. The standard spectrum described above may be an energy spectrum corresponding to the above object layer which is obtained beforehand by actual measurement or simulation using a standard sample having a known composition distribution and layer thickness in the depth direction.

When the layer thickness is calculated by the comparison with the accurate standard spectrum as described above, a highly reliable layer thickness can be expected.

In addition, when the thickness of the object layer is calculated based on the difference between the spectrum area surrounded by the waveform of the independent energy spectrum and that surrounded by the waveform of the standard energy spectrum obtained beforehand, the layer thickness of the object layer can be relatively evaluated.

Furthermore, the spectrum area described above may correspond to the total number of scattered particle counts in a predetermined energy spectrum such as the above theoretical spectrum, measured spectrum, or independent spectrum.

As described above, in the present invention, energy of the scattered particles is measured which are scattered in the direction of a specific scattering angle at which an energy spectrum corresponding to the object layer independently appears, the independent energy spectrum of the object layer is extracted which independently appears in the measured energy spectrum obtained by this measurement, and the thickness of the object layer is calculated based on the spectrum area surrounded by the waveform of the independent energy spectrum thus extracted. Since the analysis of the thickness is not performed using the half value width but is performed based on the spectrum area, highly accurate analysis can be realized. In addition, even in the case of a thin film layer or a thin film sample having a small number of counts, the layer thickness is calculated based on the spectrum area, and hence a highly accurate analysis can be performed. Furthermore, without using the fitting method which depends on personal knowledge, experience, and the like, since the thickness of the object layer can be calculated by simulation using a computer (simulator), processing capacity in the entire analysis can be improved.

DESCRIPTION OF THE PREFERRED EMBODIMENTS

Hereinafter, with reference to the figures, the embodiments of the present invention will be described so as to facilitate understanding of the present invention. The following embodiments are particular examples of the present invention and do not limit the technical scope of the present invention at all.

A spectrum analysis method of the embodiment according to the present invention may be applied to the HRBS analyzer A already described with reference to FIGS. 1 and 2 and relates to a method for analyzing the composition distribution in the depth direction of the sample 2, which is composed of a single layer or multiple layers, based on a measured spectrum measured by the HRBS analyzer A. The HRBS analyzer A is merely one example of a sample analyzer measuring an energy spectrum of scattered ions (scattered particles) scattered at the sample 2 by irradiation with ion beams, and the spectrum analysis method of the present invention may be applied to an analyzer using ions as a prove, such as an ERD analyzer analyzing the composition of a sample based on an energy spectrum of recoil ions or a secondary ion mass spectrometric analyzer based on surface sputtering.

With reference to a flowchart shown in FIG. 5, there will be described one example of a procedure measuring (calculating) the thickness of an object layer of the sample by a spectrum analysis method of the embodiment according to the present invention. This spectrum analysis method can be performed in accordance with the procedure shown in the flowchart. In this embodiment, the sample 2 which is to be analyzed is a thin film having a three-layered structure composed of a layer 51 of a heavy element P, a layer 52 of a light element Q, and a layer 53 of a heavy element P provided in that order from the top, and the layer 52 provided as a middle layer is the object layer to be analyzed. In the figure, S1, S2, and so on indicate steps of the procedure.

Figure 6:
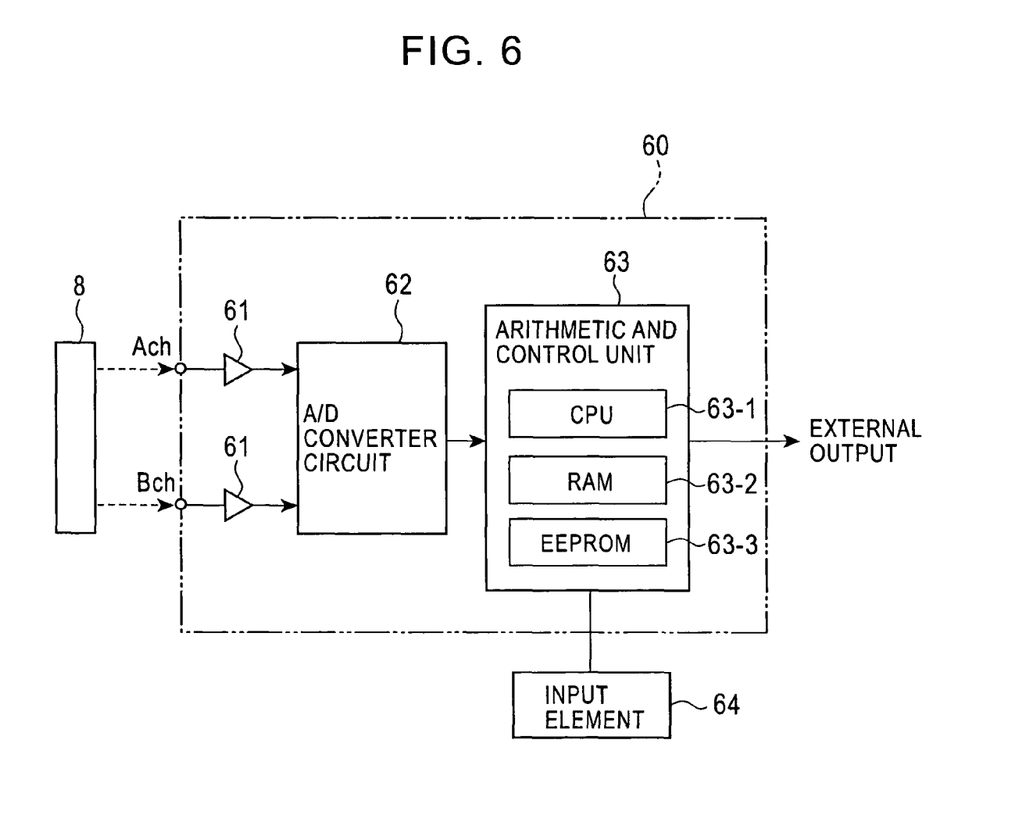
FIG. 6 is a block diagram showing a schematic structure of a simulator 60 which is one example of a spectrum analyzer according to an embodiment of the present invention.

First, based on a predefined distribution defined beforehand for the sample 2 in the depth direction, theoretical spectra corresponding to predetermined scattering angles of the scattered ions (scattered particles) are obtained by simulation using a simulator 60 (one example of a spectrum analyzer) having the structure shown by a block diagram in FIG. 6 (S1: theoretical spectrum-obtaining step). The predefined distribution described above is a composition distribution (element distribution) defined for the sample 2 in the depth direction. That is, in this embodiment, the predefined distribution indicates the composition distribution (layers 51, 52, and 53) of the sample 2. Since the predefined distribution as described above is set and registered beforehand in the simulator 60, based on the predefined distribution, simulation of theoretical spectra corresponding to all angles which can be set as the scattering angle can be executed in the simulator 60. In order to improve the processing capacity of the simulator 60, simulation may be executed at predetermined angle intervals (such as every 10° intervals).

The above simulator 60 is one example of a spectrum analyzer realizing this spectrum analysis method, in which a measured spectrum of scattered ions incident on the detector 8 can be obtained, and a theoretical spectrum can be obtained based on an input data or the like by simulation. As shown in the block diagram of FIG. 6, this simulator 60 is composed of a plurality of channels (A channel, B channel, and the like) detecting the positions of scattered ions incident on (reaching) the detector 8, amplifiers 61 amplifying detection signals of the scanned ions detected by the channels, an A/D converter circuit 62 digitizing the detection signals amplified by the amplifier 61, and an arithmetic and control unit 63 executing arithmetic processing based on the digitalized detection signals and equations (1) to (4). In addition, an input element 64 such as a keyboard or a mouse is connected to the arithmetic and control unit 63, and by operation of this input element 64, data (information) or commands (instruction) used for the arithmetic processing in the arithmetic and control unit 63 are input (set). The results (such as measured spectra and/or spectra obtained by simulation) are output by the arithmetic and control unit 63 to an external output device (not shown) such as a printer or a CRT connected to the arithmetic and control unit 63.

The arithmetic and control unit 63 is composed of a CPU 63-1 (central processing unit), a RAM 63-2, an EEPROM 63-3, and the like. This EEPROM 63-3 stores arithmetic results, arithmetic programs based on the above equations, various data or commands input from the input element 64 to be used for the arithmetic processing, and the like, and by the CPU 63-1, the data, commands, and arithmetic programs are read, so that the arithmetic processing is executed in the RAM 63-2 based on the arithmetic programs.

Figure 7A:
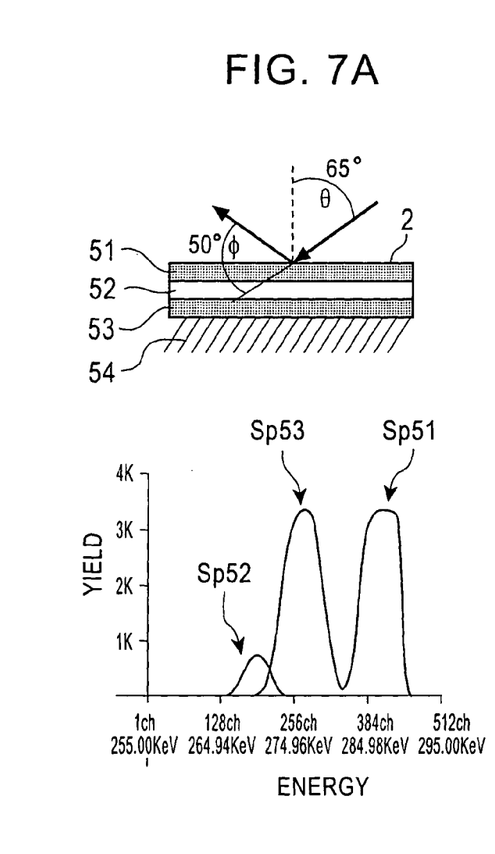
FIGS. 7A to 7C are spectrum views each showing a theoretical spectrum obtained by simulation.
Figure 7B:
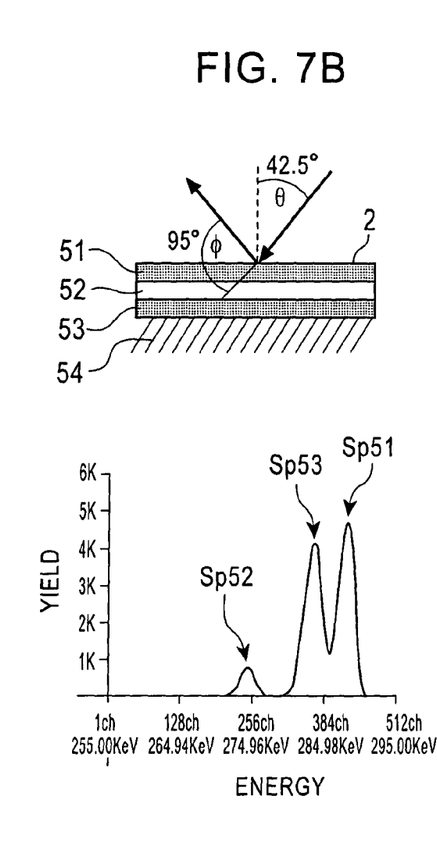
Figure 7C:
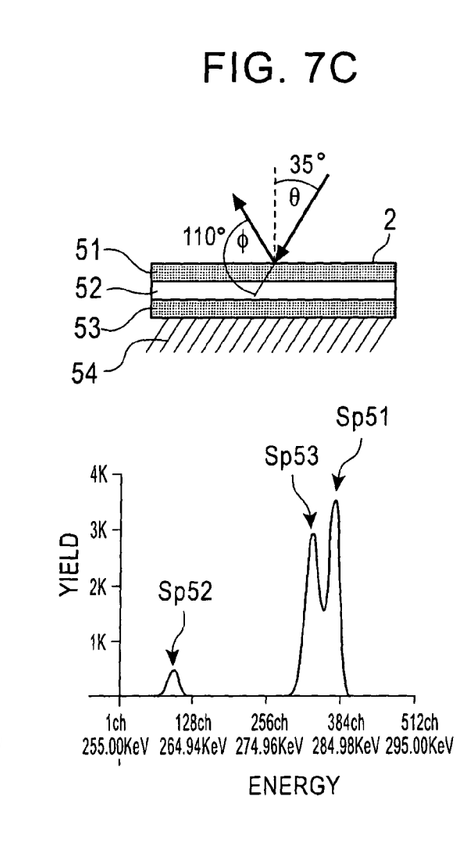

Examples of the theoretical spectra obtained by simulation using the simulator 60 are shown in FIGS. 7A to 7C. The theoretical spectrum thus obtained is displayed on a display screen or the like connected to the simulator 60. In this embodiment, in order to simplify the description thereof, an example will be described in which theoretical spectra corresponding to three scattering angles are obtained; however, of course, the present invention is not limited thereto. A theoretical spectrum at a scattering angle φ of 50° (incident angle θ: 65°), a theoretical spectrum at a scattering angle φ of 95° (incident angle θ: 42.5°), a theoretical spectrum at a scattering angle φ of 110° (incident angle θ: 35°) are shown in FIGS. 7A, 7B, and 7C, respectively, and Sp51, Sp52, and Sp53 in the figure represent the spectra corresponding to the layer 51, the object layer 52 which is to be analyzed, and the layer 53, respectively.

When the theoretical spectra (theoretical spectra shown in FIGS. 7A, 7B, and 7C) are obtained in Step Si, subsequently, a scattering angle (corresponding to the specific scattering angle) at which the spectrum corresponding to the object layer 52 independently appears in the theoretical spectrum thus obtained is searched (S2: scattering angle-searching step). That is, processing is performed so as to find out the scattering angle at which the spectrum Sp52 independently appears in each of the theoretical spectra shown in FIGS. 7A to 7C. As the procedure of Step S2, the search may be automatically executed by simulation using the simulator 60; however, in this embodiment, the most suitable theoretical spectrum is manually searched from a plurality of theoretical spectra displayed on a display screen or the like, and subsequently, a scattering angle corresponding to one theoretical spectrum selected by input using the keyboard and the mouse of the input element 64 is determined as the specific scattering angle.

In this step, when the spectrum Sp52 independently appears as shown in FIGS. 7B and 7C (Yes side of Step S3), a scattering angle of 95° or 110° is determined as the specific scattering angle. Either one of the above two scattering angles may be determined as the specific scattering angle; however, in order to obtain a high analysis accuracy, a scattering angle φ at which a spectrum is obtained having a large number of counts and/or higher energy of scattered ions is preferably determined as the specific scattering angle. Hence, in this embodiment, as the specific scattering angle, a scattering angle of 95° at which the theoretical spectrum shown in FIG. 7B is obtained is determined as the specific scattering angle. Information relating to a specific scanning angle of 95° thus determined is stored in the EEPROM 63-3 of the simulation 60.

On the other hand, when a theoretical spectrum in which the spectrum Sp52 independently appears cannot be found out, subsequently, the processing is finished (No side of Step S3). Of course, in accordance with the procedure from Step S1, the specific scattering angle may again be searched by changing the scattering angle.

Next, in the HRBS analyzer A, after the scattering angle is set to 95° by moving and operating the electromagnetic spectrometer Z, the goniometer 21 and the like, energy of scattered ions scattered in the direction of a scattering angle of 95° thus set is actually measured, so that the measured spectrum is obtained (S4: measured spectrum-obtaining step). That is, the measured spectrum of the energy of scattered particles is obtained which are scattered in the direction of a specific scattering angle of 95° at which the spectrum corresponding to the object layer 52 independently appears. As described above, the arithmetic and control unit 63 which executes arithmetic operation of the measured spectrum based on the detection signals from the detector 8 corresponds to the measured spectrum-obtaining means.

Figure 8:
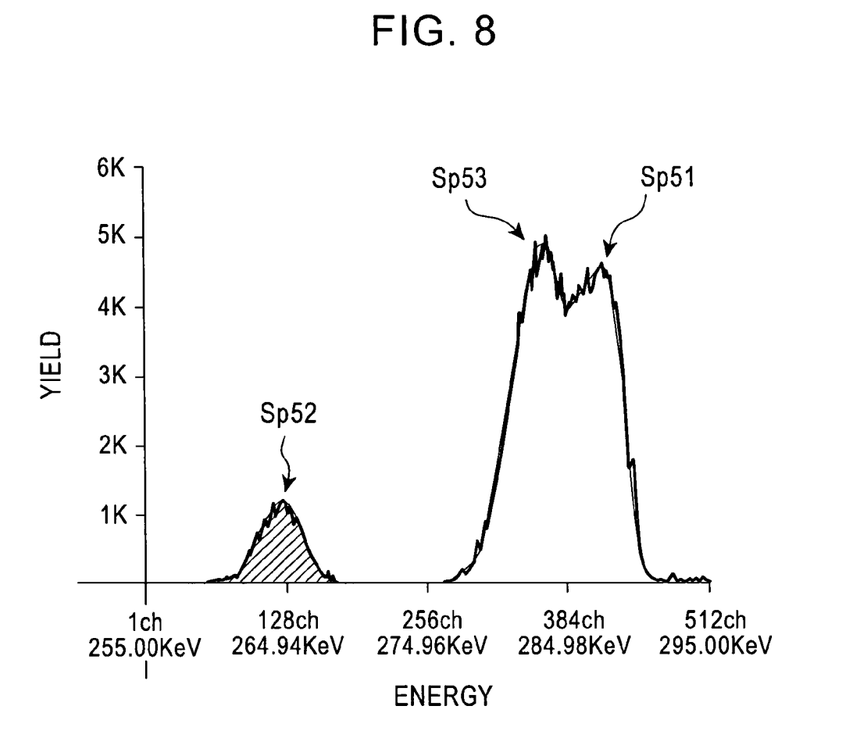
FIG. 8 is a spectrum view showing a measured spectrum of the sample 2 measured by the HRBS analyzer A.

The measured spectrum corresponding to a scattering angle of 95° obtained as described above is shown in FIG. 8. Between the measured spectrum shown in FIG. 8 and the theoretical spectrum shown in FIG. 7B obtained by simulation, the waveforms are slightly different, and this difference is caused, for example, by the thicknesses of the layers 51, 52, and 53 of the sample 2.

Subsequently, by the simulator 60 (see FIG. 6), processing is performed in which the spectrum (hereinafter referred to as "independent spectrum") of the object layer 52 which independently appears in the measured spectrum obtained in Step S4 is extracted (S5: independent spectrum-extraction step). For example, from a plurality of measured spectra obtained by the simulator 60 and displayed on a display screen or the like, by manual input using the keyboard and the mouse of the input element 64, processing for selecting one independent spectrum is executed. The processing described above is performed by the arithmetic and control unit 63, and the arithmetic and control unit 63 in this step corresponds to the independent spectrum-extraction means.

Next, a spectrum area (oblique portion in FIG. 8) surrounded by the waveform of the independent spectrum Sp52 thus extracted is calculated by known integration arithmetic operation or the like by the arithmetic and control unit 63 (S6), and based on the spectrum area thus calculated, the thickness of the object layer 52 is calculated by simulation (S7) (S6 and S7: layer thickness-calculating step). The arithmetic and control unit 63 calculating the thickness of the object layer 52 by the simulation as described above corresponds to the layer thickness-calculating means. In this embodiment, an example will be described in which the spectrum area described above is calculated; however, as another example, after the total number of scattered ion counts of the independent spectrum Sp52 is obtained, the thickness of the object layer 52 may be calculated based on the total number of counts thus obtained.

As a calculation example in Step S7, for example, it may be considered that the thickness of the object layer 52 is calculated by comparing the spectrum area surrounded by the waveform of the independent spectrum Sp52 with the spectrum area surrounded by the waveform of a standard energy spectrum (hereinafter referred to as "standard spectrum") obtained beforehand. The standard spectrum described above is a spectrum corresponding to the object layer 52 which is obtained beforehand by simulation or by actual measurement using a standard sample which has the same composition distribution as that of the sample 2 (that is, the standard sample has a known composition distribution) and is composed of layers each having a known thickness. Since the layer thickness is obtained by comparison with the accurate standard spectrum, the calculated value thus obtained is highly reliable. In this case, the standard spectrum and the independent spectrum Sp52 cannot directly be compared with each other since the amount of incident ions in measurement, the measurement time and the like are different from each other. Hence, before the spectrum area of the independent spectrum Sp52 is calculated, known calibration processing must be performed based on the spectrum of a silicon substrate 54, the number of counts thereof or the like so that the independent spectrum Sp52 and the standard spectrum may be compared with each other based on the same criterion.

Particular simulation processing in Step S7 is processing performed using equations (1) to (4) and the known data such as the stopping coefficient ε and energy of incident ions, which are stored beforehand in the simulator, and since the processing itself is not different from related simulation processing for calculating the layer thickness based on the half value width, the description in detail will be omitted.

Figure 9:
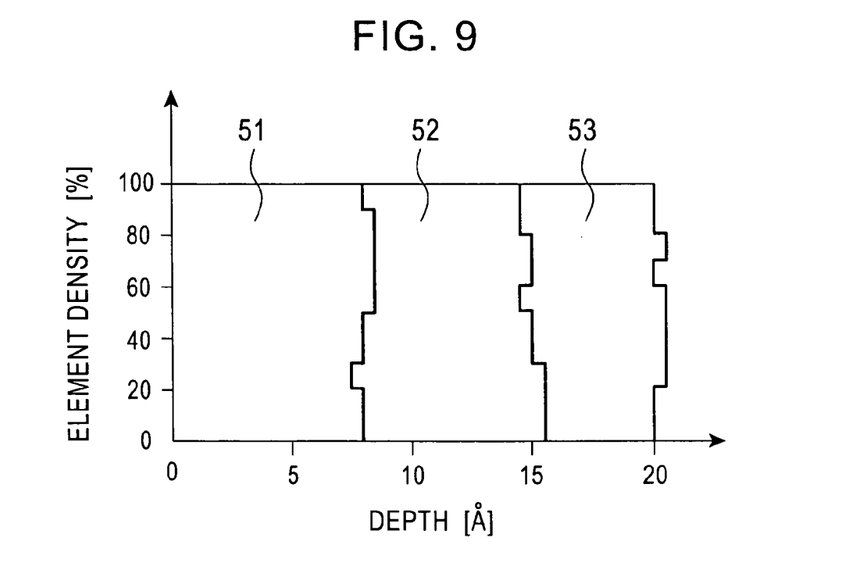
FIG. 9 is a view showing an element profile of a sample obtained by simulation.

In the above description, although the method for obtaining the thickness of the object layer 52 has been described, of course, the thicknesses of the layers 51 and 53 of the sample 2 may be obtained as the object layer by the same method as described above. FIG. 9 shows an element profile reflecting the thicknesses of the respective layers of the sample 2 obtained as described above.

As described above, heretofore, the thickness of the object layer has been calculated by simulation based on the half value width (shown by the double sided arrow in FIG. 4) of the measured spectrum; however, according to the present invention, since the thickness of the object layer is calculated by simulation based on the spectrum area, even in the case of a thin film layer or a thin film sample having a small number of counts (measured yield), the thickness of the object layer can be accurately calculated without using the fitting method, and as a result, processing capacity in the entire analysis can be improved.

EXAMPLE 1

Figure 10:
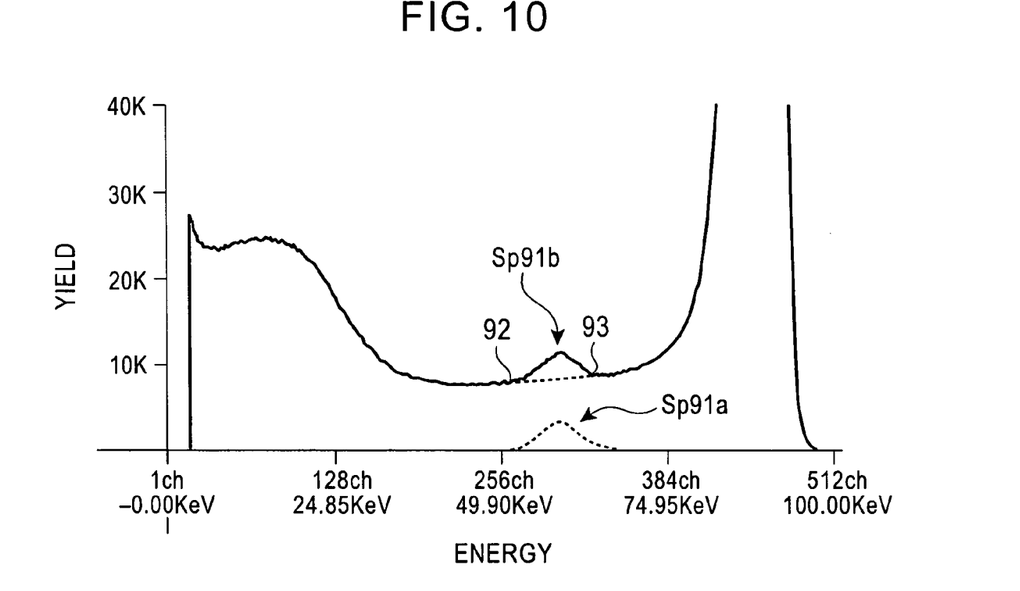
FIG. 10 is a spectrum view showing one example of the spectrum of a sample having a multilayer structure.

In the above embodiment, the spectrum analysis method has been described in which the sample 2 having a three-layered structure is used as the object for analysis; however, the analysis is actually performed for a thin film sample composed of many layers. Hence, unlike the theoretical spectra shown in FIGS. 7A to 7C, the independent spectrum of the object layer may not be obtained in many cases. In the case described above, according to the above description, since the independent spectrum cannot be extracted, the processing is finished in Step S3. However, for example, as shown in FIG. 10, when a spectrum Sp91b corresponding to an independent spectrum Sp91a of the object layer appears in the theoretical spectrum obtained by simulation, after the measured spectrum is obtained by regarding this scattering angle as the specific scattering angle, the spectrum 91a is extracted, the layer thickness can then be obtained. In this case, as the extraction processing in Step S5, various methods may be considered such as a method in which the spectrum Sp91b is extracted by detecting the inflection points, that is, points 92 and 93 shown in the figure, of the waveform depending on whether the steepness of the waveform of the measured-spectrum is a predetermined value or more.

EXAMPLE 2

Figure 11:
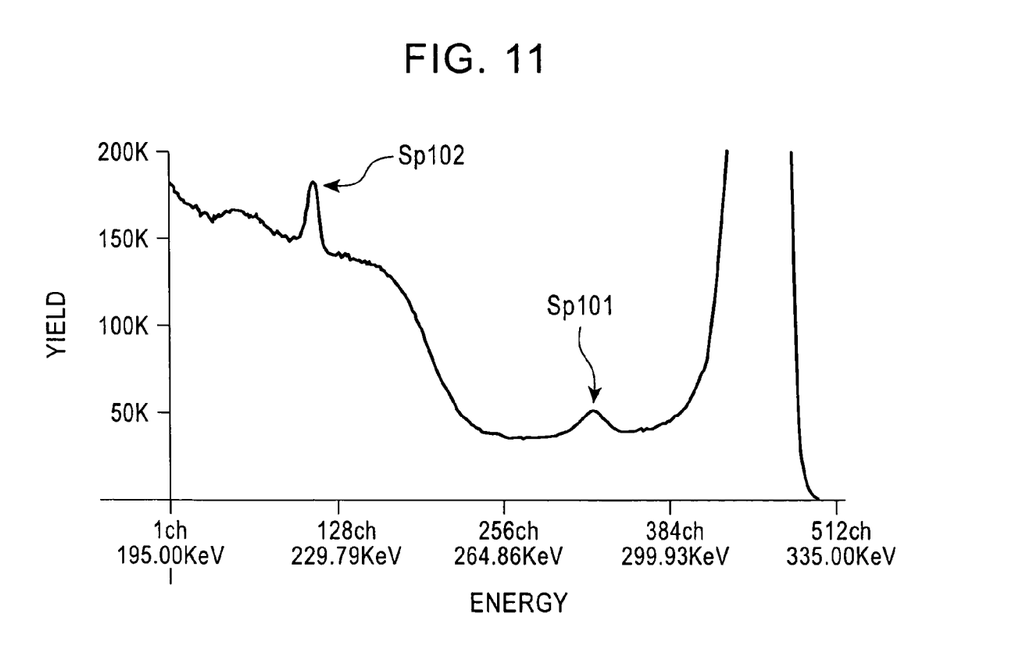
FIG. 11 is a spectrum view showing one example of a spectrum obtained from a predetermined oxide.

In addition, in the above embodiment, the spectrum analysis method has been described in which the sample 2 composed of thin layers each containing one element is used as the object for analysis; however, the case in which the object layer is composed of a plurality of elements (oxide, sulfide, fluoride, or the like) may also be considered in some cases. From this type of compound, a spectrum including peaks associated with respective elements contained in the compound can be obtained. A spectrum obtained from an oxide of a light element is shown in FIG. 11. In the figure, a spectrum Sp101 corresponds to the light element, and a spectrum Sp102 corresponds to an oxygen atom. In this case, although the thickness of the object layer formed of the compound can be obtained from either one of the spectrum areas, in order to improve the accuracy of the measurement, the thickness of the object layer may be obtained from both spectrum areas surrounded by the respective waveforms of the spectrum Sp101 and spectrum Sp102.

EXAMPLE 3

Figure 5:
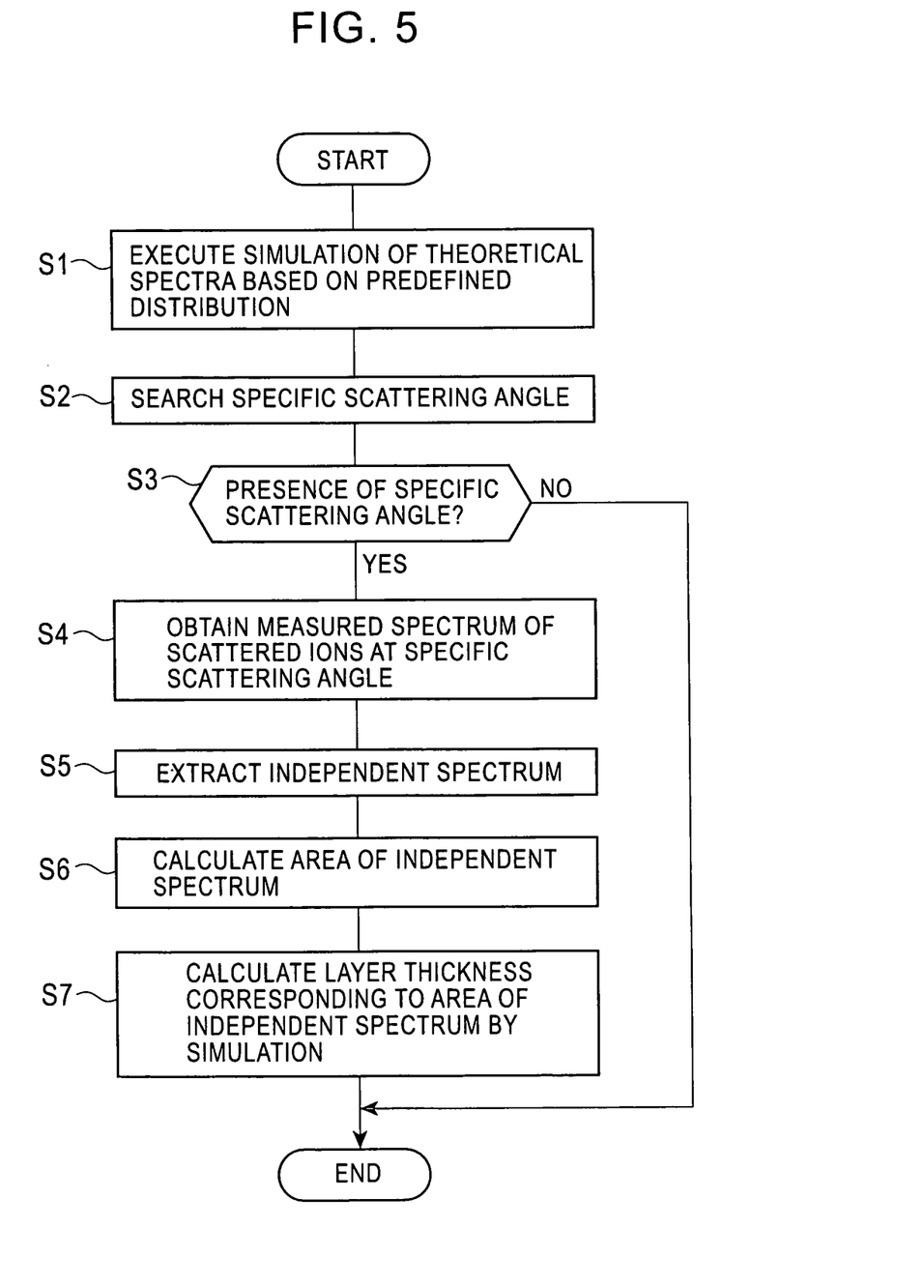
FIG. 5 is a flowchart illustrating one example of a procedure of the spectrum analysis method.
Figure 12A:
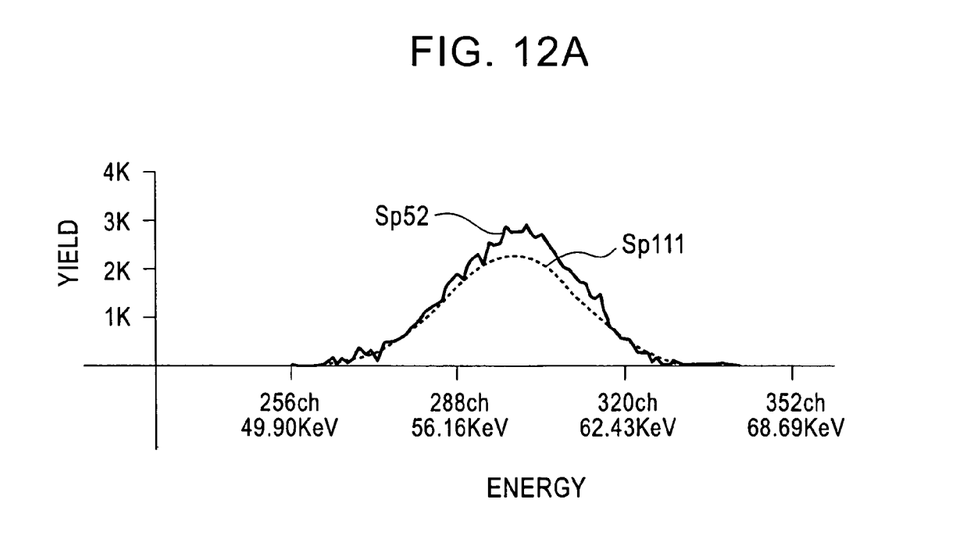
FIG. 12A is a spectrum view in which a standard spectrum Sp111 and an independent spectrum Sp52 are overlapped.

In the above embodiment, the thickness of the object layer 52 is calculated by comparing the spectrum area of the independent spectrum Sp52 with that of the standard spectrum in Step S7 (see FIG. 5). One example of this comparison, it may also be considered to calculate the thickness of the object layer 52 based on the difference between the spectrum area of the independent spectrum Sp52 and that of the standard spectrum. In FIG. 12A, a standard spectrum Sp111 and the independent spectrum Sp52 overlapped with each other are shown, and in FIG. 12B, a difference spectrum Sp112 between the standard spectrum Sp111 and the independent spectrum Sp52 is shown.

Figure 12B:
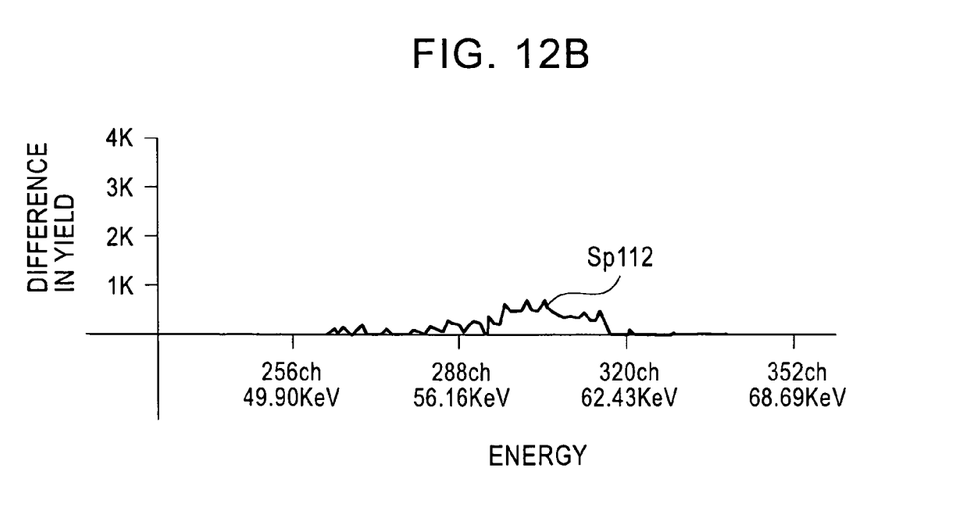
FIG. 12B is a spectrum view showing a difference component spectrum Sp112 between the standard spectrum Sp111 and the independent spectrum Sp52.

The spectrum area of the difference spectrum Sp112 shown FIG. 12B indicates the difference in thickness between the object layer 52 and the layer of the standard sample corresponding thereto. Accordingly, since the spectrum area of the difference spectrum Sp112 thus obtained is provided with a negative or a positive sign, it is accurately determined based on the sign described above whether the thickness of the object layer 52 is larger or smaller than the standard thickness. In addition, depending on whether the difference in thickness calculated based on equation (5) below is in a predetermined range or not, the manufacturing accuracy of the sample can also be verified.

$$\Delta t = \frac{S_1 - S_0}{S_0} \times T \tag{5}$$

In equation (5), $\Delta t$ indicates the difference in thickness, $S_o$ indicates the spectrum area of the standard spectrum Sp112, $S_1$ indicates the spectrum area of the independent spectrum Sp52, and T indicates the standard thickness.

What is claimed is:

1. A spectrum analyzer analyzing a composition distribution of a sample in the depth direction based on an energy spectrum of scattered particles scattered at the sample by irradiation with ion beams, the sample including at least one object layer to be analyzed which contains at least one element, said spectrum analyzer comprising:

an ion beam generator;

scattering angle-setting means for setting a scattering angle of ion beams which are emitted from said ion beam generator and which are scattered at the sample, including a simulator for obtaining specific scattering angles where an independent energy spectrum of said at least one element of the object layer independently appears, and setting the scattering angle according to the specific scattering angles;

measured spectrum-obtaining means for obtaining a measured energy spectrum by measuring energy of scattered particles scattered in the direction of the scattering angle set by said scattering angle-setting means, the scattered particles being scattered from the sample when the sample is irradiated with the ion beams;

independent spectrum-extraction means for extracting an independent energy spectrum of said at least one element of the object layer which independently appears in the measured energy spectrum obtained by said measured spectrum-obtaining means;

means for obtaining a standard energy spectrum of a standard sample having a known composition distribution and layer thickness in the depth direction; and layer thickness-calculation means for calculating the thickness of the object layer based on a spectrum area surrounded by the waveform of the independent energy spectrum extracted by said independent spectrum-extraction means, wherein said layer thickness-calculation means calculates the thickness of the object layer by comparing the spectrum area surrounded by the waveform of the independent energy spectrum with a spectrum area surrounded by the waveform of the standard energy spectrum.

2. The spectrum analyzer according to claim 1, wherein said scattering angle-determining means comprises:

theoretical spectrum-display means for displaying the theoretical spectra; and input means for performing input to select one of the theoretical spectra displayed by said theoretical spectrum-display means.

3. The spectrum analyzer according to claim 1, wherein the object layer contains a plurality of elements, and said layer thickness-calculation means calculates the thickness of the object layer based on spectrum areas surrounded by the waveforms of the independent energy spectra of the respective elements.

4. The spectrum analyzer according to claim 1, wherein the standard energy spectrum is obtained by simulation or actual measurement of the standard sample and is an energy spectrum corresponding to the object layer.

5. The spectrum analyzer according to claim 1, wherein said layer thickness-calculation means calculates the thickness of the object layer based on the difference between the spectrum area surrounded by the waveform of the independent energy spectrum and the spectrum area surrounded by the waveform of the standard energy spectrum.

6. The spectrum analyzer according to claim 1, wherein the spectrum area corresponds to the total number of scattered particle counts of the independent energy spectrum.

7. A spectrum analysis method for analyzing a composition distribution of a sample in the depth direction based on an energy spectrum of scattered particles scattered at the sample by irradiation with ion beams, the sample including at least one object layer to be analyzed, the spectrum analysis method comprising:

a step of obtaining specific scattering angles where an independent energy spectrum of said at least one element of the object layer independently appears;

a measured spectrum-obtaining step of obtaining a measured energy spectrum by measuring energy of scattered particles scattered in the direction of one of the specific scattering angles at which an energy spectrum corresponding to the object layer independently appears;

an independent spectrum-extraction step of extracting an independent energy spectrum of the object layer which independently appears in the measured energy spectrum obtained by the measured spectrum-obtaining step;

a step of obtaining a standard energy spectrum of a standard sample having a known composition distribution and layer thickness in the depth direction; and a layer thickness-calculation step of calculating the thickness of the object layer based on a spectrum area surrounded by the waveform of the independent energy spectrum extracted by the independent spectrum-extraction step, wherein said layer thickness-calculation step calculates the thickness of the object layer by comparing the spectrum area surrounded by the waveform of the independent energy spectrum with a spectrum area surrounded by the waveform of the standard energy spectrum, wherein the specific scattering angle is searched by a process comprising:

a theoretical spectrum-obtaining step of obtaining theoretical energy spectra corresponding to predetermined scattering angles of the scattered particles by simulation based on a predefined distribution set beforehand for the sample in the depth direction; and a scattering angle-searching step of searching the scattering angle at which the energy spectrum corresponding to the object layer independently appears in the theoretical energy spectra obtained by the theoretical spectrum-obtaining step.

* * * * *